US00PP12512P2

(12) United States Plant Patent
Vandenberg et al.

(10) Patent No.: US PP12,512 P2
(45) Date of Patent: Apr. 2, 2002

(54) CHRYSANTHEMUM PLANT NAMED 'YOGRACELAND'

(75) Inventors: Cornelis P. Vandenberg, Salinas, CA (US); Wendy R. Bergman, Lehigh Acres, FL (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 09/594,755

(22) Filed: Jun. 16, 2000

(51) Int. Cl.[7] ..... A01H 5/00
(52) U.S. Cl. ..... Plt./297

(58) Field of Search ..... Plt./297, 286, 294

*Primary Examiner*—Howard J. Locker
(74) *Attorney, Agent, or Firm*—C. A. Whealy

(57) ABSTRACT

A distinct cultivar of Chrysanthemum plant named 'Yograceland', characterized by its upright, somewhat spreading, and uniformly mounded plant habit; strong, dark green foliage; uniform flowering response; early flowering, eight-week response time; very large single anemone-type inflorescences that are about 13.7 cm in diameter; very light pink ray florets and yellow-tipped disc florets; and good postproduction longevity with inflorescences maintaining good substance and color for about three weeks in an interior environment.

1 Drawing Sheet

BACKGROUND OF THE INVENTION

The present Invention relates to a new and distinct cultivar of Chrysanthemum plant, botanically known as *Dendranthema grandiflora* and hereinafter referred to by the cultivar name Yograceland.

The new Chrysanthemum is a product of a planned breeding program conducted by the Inventors in Salinas, Calif. and Fort Myers, Fla. The objective of the breeding program is to create new potted Chrysanthemum cultivars with desirable inflorescence form and floret colors and good postproduction longevity.

The new Chrysanthemum originated from a cross made by the Inventors in February, 1995, in Salinas, Calif., of a proprietary Chrysanthemum seedling selection identified as YB-5899 as the male, or pollen, parent with the Chrysanthemum cultivar Blush, disclosed in U.S. Plant Pat. No. 7,985 as the female, or seed, parent. The new Chrysanthemum was discovered and selected by the Inventors in April, 1996, as a single flowering plant within the progeny of the stated cross grown in a controlled environment in Fort Myers, Fla. The selection of this plant was based on its desirable inflorescence form and floret colors and good postproduction longevity.

Asexual reproduction of the new Chrysanthemum by vegetative tip cuttings was first conducted in Fort Myers, Fla. in June, 1996. Asexual reproduction by cuttings has shown that the unique features this new Chrysanthemum are stable and reproduced true to type in successive generations.

SUMMARY OF THE INVENTION

The cultivar Yograceland has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Yograceland'. These characteristics in combination distinguish 'Yograceland' as a new and distinct Chrysanthemum:

1. Upright, somewhat spreading, and uniformly mounded plant habit.

2. Strong, dark green foliage.

3. Uniform flowering response.

4. Early flowering, eight-week response time.

5. Very large single anemone-type inflorescences that are about 13.7 cm in diameter.

6. Very light pink ray florets and yellow-tipped disc florets.

7. Good postproduction longevity with inflorescences maintaining good substance and color for about three weeks in an interior environment.

Plants of the new Chrysanthemum differ from plants of the cultivar, Pink Blush, disclosed in U.S. Plant Pat. No. 9,444, in the following characteristics:

1. Plants of the new Chrysanthemum have single anemone-type inflorescences whereas plants of the cultivar Pink Blush have single daisy-type inflorescences.

2. Plants of the new Chrysanthemum are taller than plants of the cultivar Pink Blush.

3. Plants of the new Chrysanthemum flower about two or three days earlier than plants of the cultivar Pink Blush.

BRIEF DESCRIPTION OF THE PHOTOGRAPHS

The accompanying colored photographs illustrate the overall appearance of the new Chrysanthemum showing the colors as true as it is reasonably possible to obtain in colored reproductions of this type. Colors in the photographs may differ from the color values cited in the detailed botanical description which more accurately describe the actual colors of the new Chrysanthemum.

The photograph at the top of the sheet comprises a top perspective view of a typical flowering plant of 'Yograceland'.

The photograph at the bottom of the sheet comprises a close-up view of typical inflorescences of the cultivar Yograceland.

DETAILED BOTANICAL DESCRIPTION

In the following description, color references are made to The Royal Horticultural Society Colour Chart except where general terms of ordinary dictionary significance are used. The following observations and measurements describe plants grown and flowered during the Spring in Salinas, Calif. and Leamington, Ontario, Canada, under greenhouse conditions which approximate those generally used in commercial potted Chrysanthemum production. Four unrooted cuttings were directly stuck in a 15-cm container and pinched once. Plants used for this description were grown as disbud-types. Measurements and numerical values represent averages of typical flowering plants.

Botanical classification: *Dendranthema grandiflora* cultivar Yograceland.

Commercial classification: Single anemone-type potted Chrysanthemum.

Parentage:

*Male, or pollen, parent.*—Proprietary Chrysanthemum seedling selection identified as YB-5899.

*Female, or seed, parent.*—*Dendranthema grandiflora* cultivar Blush, disclosed in U.S. Plant Pat. No. 7,985.

Propagation:

*Type.*—Terminal tip cuttings.

*Time to rooting.*—Seven to ten days with soil temperatures of 21° C.

*Rooting habit.*—Fine, fibrous and well-branched.

Plant description:

*Appearance.*—Herbaceous single anemone-type potted Chrysanthemum that is typically grown as a disbud-type. Inverted triangle; stems mostly upright and somewhat outwardly spreading giving a uniformly mounded appearance to the plant. About three lateral branches develop after removal of terminal apex (pinching). Moderate vigor.

*Plant height.*—About 27 cm.

*Plant width.*—About 37 cm.

*Lateral branches.*—Length: About 15 cm. Diameter: About 3.5 mm. Internode length: About 1.2 cm. Strength: Flexible, but strong. Texture: Pubescent. Color: 144A.

*Foliage description.*—Arrangement: Alternate. Quantity per lateral stem: About 12. Length: About 4.7 cm. Width: About 3.8 cm. Apex: Mucronate. Base: Mostly truncate. Margin: Palmately lobed, sinuses between lateral lobes parallel to overlapping. Texture: Upper and lower surfaces with very fine pubescence; veins prominent on lower surface. Color: Young foliage upper surface: 147A. Young foliage lower surface: 147B. Mature foliage upper surface: 147A. Mature foliage lower surface: 147B. Venation upper surface: 147B. Venation lower surface: 147B. Petiole length: About 1.1 cm. Petiole diameter: About 2.5 mm. Petiole color: 147B to 147C.

Inflorescence description:

*Appearance.*—Single anemone-type inflorescence form with elongated oblong-shaped ray florets. Inflorescences borne on terminals above foliage. Disk and ray florets arranged acropetally on a capitulum. Not fragrant.

*Flowering response.*—Under natural conditions, plants flower in the autumn/winter in the Northern Hemisphere. At other times of the year, inflorescence initiation and development can be induced under short day/long night conditions (at least 13.5 hours of darkness). Plants exposed to three weeks of long day/short night conditions after planting followed by photoinductive short day/long night conditions flower about eight weeks later; early flowering.

*Postproduction longevity.*—Inflorescences maintain good color and substance for about three weeks in an interior environment.

*Quantity of inflorescences.*—Typically grown as a disbud-type with one inflorescence per lateral stem; about three inflorescences per plant.

*Inflorescence bud.*—Height: About 6 mm. Diameter: About 7 mm. Color: Close to 137A.

*Inflorescence size.*—Diameter: About 13.7 cm. Depth (height): About 3.4 cm. Diameter of disc: About 4.8 cm. Receptacle diameter: About 7 mm.

*Ray florets.*—Shape: Elongated-oblong. Orientation: Initially upright, then about perpendicular to stem; flat and somewhat reflexed. Length: About 6.5 cm. Width: About 1.5 cm. Apex: Rounded, mammilate or dentate. Base: Attenuate; very short corolla tube. Margin: Entire. Texture: Smooth, glabrous, satiny. Number of ray florets per inflorescence: About 28; one row. Color: When opening, upper surface: 65C to 65D or close to 69B to 69C. When opening, lower surface: 65D or 69B to 69C. Fully opened, upper surface: Close to 65C to 65D, to 62D, to close to 69B to 69C; floret color fading towards white with subsequent development. Fully opened, lower surface: 65D, lighter than 62D or 69B to 69C.

*Disc florets.*—Shape: Enlarged, flared. Apex: Five-pointed, fringed appearance. Length: About 2.2 cm. Width: Apex, about 7 mm; base, about 1 mm. Number of disc florets per inflorescence: About 183. Color: Immature: Close to 151A to 154A to 3A to 9A to 12A. Mature: Apex: Tipped with 3A to 9A or 12A. Mid-section: Throat and tube, 62D towards white. Base: Close to 151A.

*Reproductive organs.*—Androecium: Present on disc florets only. Anther color: 9A. Pollen amount: None observed. Gynoecium: Present on both ray and disc florets.

Disease resistance: Resistance to pathogens common to Chrysanthemums has not been observed on plants grown under commercial greenhouse conditions.

Seed production: Seed production has not been observed.

It is claimed:

1. A new and distinct cultivar of Chrysanthemum plant named 'Yograceland', as illustrated and described.

* * * * *

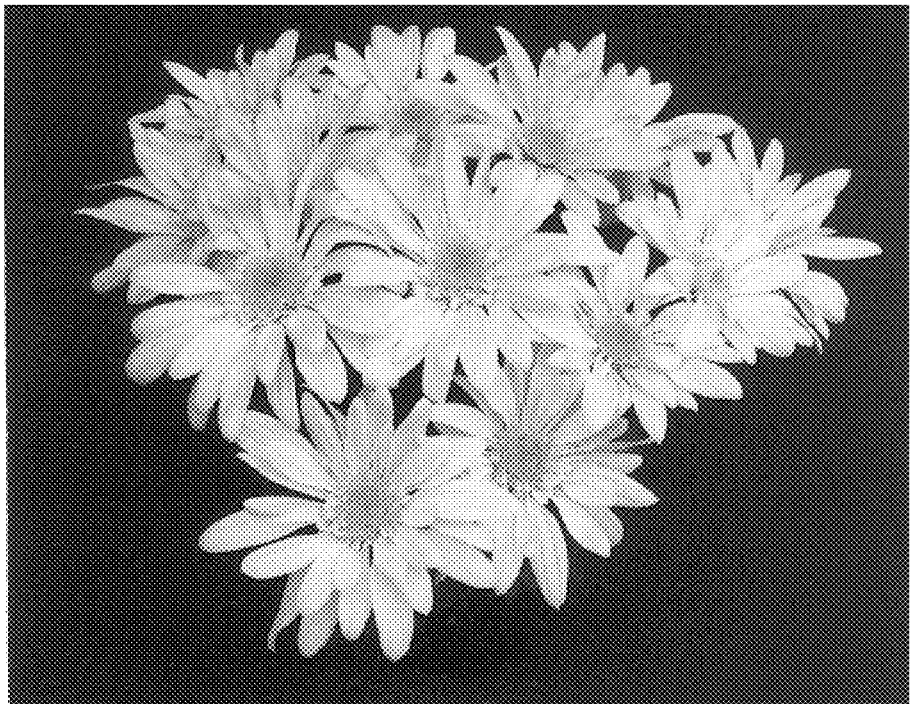
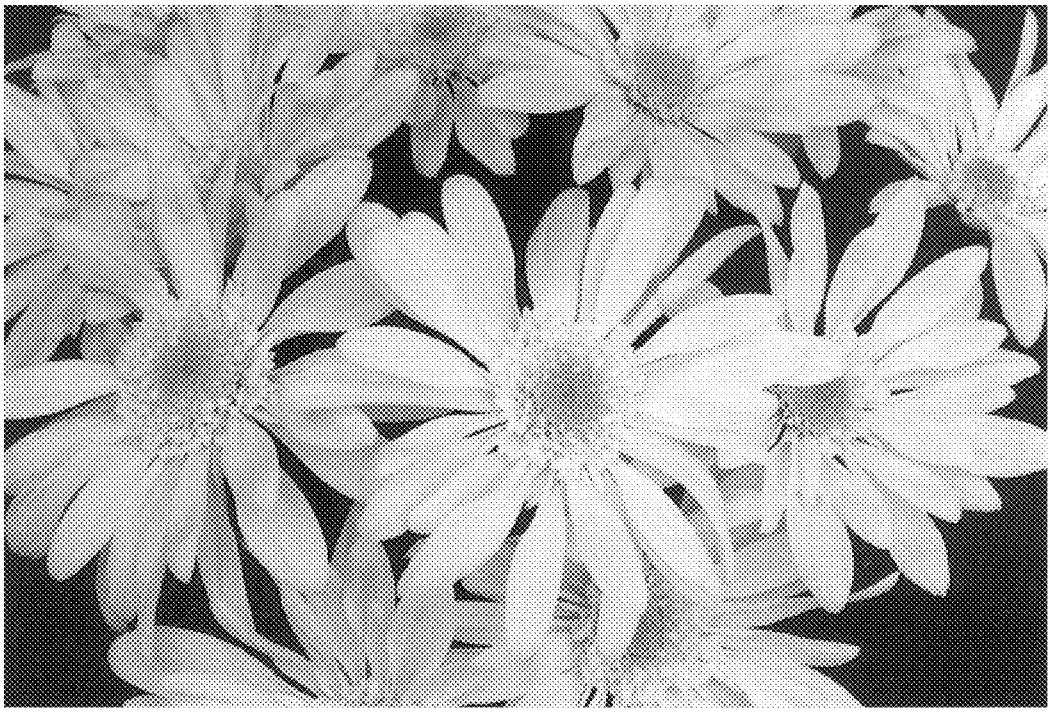

UNITED STATES PATENT AND TRADEMARK OFFICE

CERTIFICATE OF CORRECTION

PATENT NO. : PP 12,512 P2
DATED : April 2, 2002
INVENTOR(S) : Vandenberg et al.

It is certified that error appears in the above-identified patent and that said Letters Patent is hereby corrected as shown below:

Title page,
Item [*] Notice, delete the phrase "by 0 days" and insert -- by 20 days --

Signed and Sealed this

Eighteenth Day of May, 2004

JON W. DUDAS
*Acting Director of the United States Patent and Trademark Office*